United States Patent
Cristau et al.

(10) Patent No.: US 9,668,480 B2
(45) Date of Patent: Jun. 6, 2017

(54) METHOD FOR TREATING PLANTS AGAINST FUNGI RESISTANT TO FUNGICIDES USING CARBOXAMIDE OR THIOCARBOXAMIDE DERIVATIVES

(71) Applicant: BAYER CROPSCIENCE AG, Monheim (DE)

(72) Inventors: Pierre Cristau, Lyons (FR); Marie-Claire Grosjean-Cournoyer, Curis-au-Mont-d'Or (FR); Anne Lappartient, Lyons (FR); Andreas Mehl, Meerbusch (DE); Valerie Toquin, Saint-Romain-au-Mont-d'Or (FR); Francois Villalba, Abligny-sur-Saone (FR)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/434,379

(22) PCT Filed: Oct. 17, 2013

(86) PCT No.: PCT/EP2013/071734
§ 371 (c)(1),
(2) Date: Apr. 8, 2015

(87) PCT Pub. No.: WO2014/060520
PCT Pub. Date: Apr. 24, 2014

(65) Prior Publication Data
US 2015/0264927 A1    Sep. 24, 2015

Related U.S. Application Data

(60) Provisional application No. 61/730,310, filed on Nov. 27, 2012.

(30) Foreign Application Priority Data

Oct. 19, 2012    (EP) .................................... 12356021

(51) Int. Cl.
*A61K 31/695*    (2006.01)
*A01N 43/56*    (2006.01)
*A01N 55/00*    (2006.01)

(52) U.S. Cl.
CPC ............. *A01N 43/56* (2013.01); *A01N 55/00* (2013.01)

(58) Field of Classification Search
None
See application file for complete search history.

(56) References Cited

U.S. PATENT DOCUMENTS

| | | | |
|---|---|---|---|
| 8,772,266 B2 * | 7/2014 | Bartels ................ | C07D 231/16 514/341 |
| 2012/0046323 A1 | 2/2012 | Fought et al. ................ | 514/355 |
| 2012/0065164 A1 | 3/2012 | Bartels et al. ................ | 514/63 |
| 2013/0131124 A1 | 5/2013 | Greul et al. ................... | 514/355 |
| 2014/0038823 A1 | 2/2014 | Dahmen et al. .............. | 504/103 |
| 2014/0039027 A1 | 2/2014 | Görtz et al. ................... | 514/406 |
| 2014/0081030 A1 | 3/2014 | Greul et al. ................ | 548/374.1 |
| 2015/0245610 A1 | 9/2015 | Cristau et al. | |
| 2015/0250176 A1 | 9/2015 | Cristau et al. | |
| 2015/0259294 A1 | 9/2015 | Cristau et al. | |
| 2015/0264928 A1 | 9/2015 | Cristau et al. | |

FOREIGN PATENT DOCUMENTS

| | | | | |
|---|---|---|---|---|
| WO | WO 2010/130767 A2 | 11/2010 | | |
| WO | WO 2010130767 A2 * | 11/2010 | ........... | C07D 231/16 |
| WO | WO 2011/151383 A1 | 12/2011 | | |
| WO | WO 2012/013590 | 2/2012 | | |
| WO | WO 2012/110464 A1 | 8/2012 | | |
| WO | WO 2012/143127 A1 | 10/2012 | | |
| WO | WO 2014/060502 A1 | 4/2014 | | |
| WO | WO 2014/060518 A1 | 4/2014 | | |
| WO | WO 2014/060519 A1 | 4/2014 | | |
| WO | WO 2014/060521 A1 | 4/2014 | | |

OTHER PUBLICATIONS

Beresford, R. M. NZ Pesticide Resistance Management Strategy 2011, accessed from http://resistance.nzpps.org/index.php?p=fungicides/sdhi on Mar. 1, 2016.*
International Search Report issued Nov. 20, 2013 in International Application No. PCT/EP2013/071734.

* cited by examiner

Primary Examiner — Heidi Reese
(74) Attorney, Agent, or Firm — McBee Moore Woodward Vanik IP LLC

(57) ABSTRACT

The invention relates to the use of N-cyclopropyl-N-[substituted-benzyl]-3-(difluoromethyl)-5-fluoro-1-methyl-1H-pyrazole-4-carboxamide or thiocarboxamide derivatives and/or salts thereof for improving growth in crops, comprising preventively and/or curatively controlling resistant strains of fungi, particularly for controlling strains of fungi resistant to SDHI fungicides. The invention further relates to associated methods.

18 Claims, No Drawings

METHOD FOR TREATING PLANTS AGAINST FUNGI RESISTANT TO FUNGICIDES USING CARBOXAMIDE OR THIOCARBOXAMIDE DERIVATIVES

CROSS-REFERENCE TO RELATED APPLICATION(S)

The present application is a 35 U.S.C §371 national phase conversion of PCT/EP2013/071734 filed Oct. 17, 2013, which claims priority of European Application No. 12356021.1 filed on Oct. 19, 2012 and U.S Provisional Application No. 61/730,310 filed on Nov. 27, 2012. Applicants claim priority to each of the forgoing applications. The PCT International Application was published in the English language.

The invention relates to the use of N-cyclopropyl-N-[substituted-benzyl]-3-(difluoromethyl)-5-fluoro-1-methyl-1H-pyrazole-4-carboxamide or thiocarboxamide derivatives and/or salts thereof for improving growth in crops, comprising preventively and/or curatively controlling resistant strains of fungi, particularly for controlling strains of fungi resistant to SDHI fungicides, and to associated methods.

Severals fungicides are known as SDH (Succinate Dehydrogenase) Inhibitors, which describes their mode of action. The target enzyme of SDH Inhibitors is succinate dehydrogenase (so-called complex II in the mitochondrial respiration chain), which is a functional part of the tricarboxylic cycle and linked to the mitochondrial electron transport chain (Keon et al., 1991, Current Genetics 19, 475-481). SDHI (Succinate Dehydrogenase Inhibitors) fungicides were discovered more than 40 years ago, and are very efficient fungicides for controlling a broad variety of major diseases in various crops, including cereals, soybean, corn, oilseed rape and specialty crops.

But, because of their single-site specificity, these SDHI fungicides can be prone to resistance development. Even more dramatic, resistance development leads often to cross-resistance, wherein resistance to a particular SDHI fungicide results in resistance to other SDHI fungicides, to which the fungi may not have been exposed.

Strains of fungi resistant to SDH inhibitors wherein the resistance is due to mutation(s) in the fungi succinate dehydrogenase gene are already known for several fungal species and the target site mutations have been already detected both in lab generated mutants and filed studies. Considering the apparition of strains resistant to fungicides as an urge problem, and particularly strains resistant to SDHI fungicides, FRAC (Fungicide Resistance Action Committee)-SDHI working group has been created for common resistance management recommendations.

The inventors of the present invention surprisingly found that N-cyclopropyl-N-[substituted-benzyl]-3-(difluoromethyl)-5-fluoro-1-methyl-1H-pyrazole-4-carboxamide or thiocarboxamide derivatives are able to control strains of fungi resistant to other carboxamides fungicides.

N-cyclopropyl-N-[substituted-benzyl]-3-(difluoromethyl)-5-fluoro-1-methyl-1H-pyrazole-4-carboxamide or thiocarboxamide derivatives, their preparation from commercially available materials and their use as fungicides are disclosed in WO2007/087906, WO2009/016220, WO2010/130767 and EP2251331. It is also known that these compounds can be used as fungicides and mixed with other fungicides or insecticides (cf. patent applications PCT/EP2012/001676 and PCT/EP2012/001674).

It is an object of the present invention to provide a method of plant growth in order to better control fungi, particularly resistant strain of fungi, and obtain better plants, higher crop yield, better crop quality and better conditions of agricultural practices.

We have found that this object is achieved by a method for treating plants curatively and/or preventively against at least one resistant strain of fungi, comprising applying to said plants, to the seeds from which they grow or to the locus in which they grow, a non-phytotoxic, effective plant growth promoting amount of a compound having the formula I

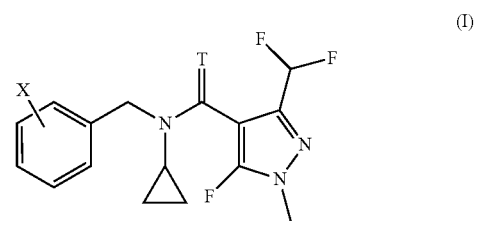

wherein T represents an oxygen or a sulfur atom and X is selected from the list of 2-isopropyl, 2-cyclopropyl, 2-tert-butyl, 5-chloro-2-ethyl, 5-chloro-2-isopropyl, 2-ethyl-5-fluoro, 5-fluoro-2-isopropyl, 2-cyclopropyl-5-fluoro, 2-cyclopentyl-5-fluoro, 2-fluoro-6-isopropyl, 2-ethyl-5-methyl, 2-isopropyl-5-methyl, 2-cyclopropyl-5-methyl, 2-tert-butyl-5-methyl, 5-chloro-2-(trifluoromethyl), 5-methyl-2-(trifluoromethyl), 2-chloro-6-(trifluoromethyl), 3-chloro-2-fluoro-6-(trifluoromethyl), 2-ethyl, 2-trimethylsilyl and 2-ethyl-4,5-dimethyl, or an agrochemically acceptable salt thereof.

Preference is given to compound of the formula (I) selected from the group consisting of:
N-cyclopropyl-3-(difluoromethyl)-5-fluoro-N-(2-isopropylbenzyl)-1-methyl-1H-pyrazole-4-carboxamide (compound A1),
N-cyclopropyl-N-(2-cyclopropylbenzyl)-3-(difluoromethyl)-5-fluoro-1-methyl-1H-pyrazole-4-carboxamide (compound A2),
N-(2-tert-butylbenzyl)-N-cyclopropyl-3-(difluoromethyl)-5-fluoro-1-methyl-1H-pyrazole-4-carboxamide (compound A3),
N-(5-chloro-2-ethylbenzyl)-N-cyclopropyl-3-(difluoromethyl)-5-fluoro-1-methyl-1H-pyrazole-4-carboxamide (compound A4),
N-(5-chloro-2-isopropylbenzyl)-N-cyclopropyl-3-(difluoromethyl)-5-fluoro-1-methyl-1H-pyrazole-4-carboxamide (compound A5),
N-cyclopropyl-3-(difluoromethyl)-N-(2-ethyl-5-fluorobenzyl)-5-fluoro-1-methyl-1H-pyrazole-4-carboxamide (compound A6),
N-cyclopropyl-3-(difluoromethyl)-5-fluoro-N-(5-fluoro-2-isopropylbenzyl)-1-methyl-1H-pyrazole-4-carboxamide (compound A7),
N-cyclopropyl-N-(2-cyclopropyl-5-fluorobenzyl)-3-(difluoromethyl)-5-fluoro-1-methyl-1H-pyrazole-4-carboxamide (compound A8),
N-(2-cyclopentyl-5-fluorobenzyl)-N-cyclopropyl-3-(difluoromethyl)-5-fluoro-1-methyl-1H-pyrazole-4-carboxamide (compound A9),
N-cyclopropyl-3-(difluoromethyl)-5-fluoro-N-(2-fluoro-6-isopropylbenzyl)-1-methyl-1H-pyrazole-4-carboxamide (compound A10),
N-cyclopropyl-3-(difluoromethyl)-N-(2-ethyl-5-methylbenzyl)-5-fluoro-1-methyl-1H-pyrazole-4-carboxamide (compound A11), N-cyclopropyl-3-(difluoromethyl)-5-fluoro-N-(2-isopropyl-5-methylbenzyl)-1-methyl-1H-pyrazole-4-carboxamide (compound A12),
N-cyclopropyl-N-(2-cyclopropyl-5-methylbenzyl)-3-(difluoromethyl)-5-fluoro-1-methyl-1H-pyrazole-4-carboxamide (compound A13),
N-(2-tert-butyl-5-methylbenzyl)-N-cyclopropyl-3-(difluoromethyl)-5-fluoro-1-methyl-1H-pyrazole-4-carboxamide (compound A14),
N-[5-chloro-2-(trifluoromethyl)benzyl]-N-cyclopropyl-3-(difluoromethyl)-5-fluoro-1-methyl-1H-pyrazole-4-carboxamide (compound A15),
N-cyclopropyl-3-(difluoromethyl)-5-fluoro-1-methyl-N-[5-methyl-2-(trifluoromethyl)benzyl]-1H-pyrazole-4-carboxamide (compound A16),
N-[2-chloro-6-(trifluoromethyl)benzyl]-N-cyclopropyl-3-(difluoromethyl)-5-fluoro-1-methyl-1H-pyrazole-4-carboxamide (compound A17),
N-[3-chloro-2-fluoro-6-(trifluoromethyl)benzyl]-N-cyclopropyl-3-(difluoromethyl)-5-fluoro-1-methyl-1H-pyrazole-4-carboxamide (compound A18).
N-cyclopropyl-3-(difluoromethyl)-N-(2-ethyl-4,5-dimethylbenzyl)-5-fluoro-1-methyl-1H-pyrazole-4-carboxamide (compound A19),
N-cyclopropyl-3-(difluoromethyl)-5-fluoro-N-(2-isopropylbenzyl)-1-methyl-1H-pyrazole-4-carbothio-amide (compound A20),
N-cyclopropyl-3-(difluoromethyl)-N-(2-ethylbenzyl)-5-fluoro-1-methyl-1H-pyrazole-4-carboxamide (compound A21), and
N-cyclopropyl-3-(difluoromethyl)-5-fluoro-1-methyl-N-[2-(trimethylsilyl)benzyl]-1H-pyrazole-4-carboxamide (compound A22).

In the context of the invention a "resistant strain of fungi" means a mutated strain of fungi which is resistant to a fungicide when the wild-type of this strain is sensitive to said fungicide, when the fungicide is used at the usual rate of utilisation. The resistance can be due to a mutation in the gene encoding the target of the fungicide.

In a particular embodiment of the invention, compound of formula (I) or salt thereof are used for treating plants curatively and/or preventively against at least one resistant strain of fungi which is resistant to at least one SDHI (succinate dehydrogenase inhibitor) fungicide. Said "resistant strain of fungi" is a mutated strain of fungi which is resistant to at least one SDHI fungicide, when the wild-type of this strain is sensitive to said fungicide. The resistance may be a cross-resistance, which results in resistance to several SDHI fungicides, which may be from similar chemical classes, and/or may have the same target and/or binding site. The resistance is generally due to a mutation in the gene encoding the target of the SDHI fungicide, i.e. in the fungi succinate dehydrogenase gene.

The target enzyme of SDHI fungicides is succinate dehydrogenase (SDH, so-called complex II in the mitochondrial respiration chain) which is a functional part of the tricarboxylic cycle and linked to the mitochondrial electron transport chain. SDH consists of four subunits (A, B, C and D) and the binding site of ubiquitone (and SDHIs) is formed by the subunits B, C and D.

SDHI fungicides belong generally to two classes of compounds, i.e. benzamide derivatives or carboxamide derivatives. Cases of resistance and often cross-resistance of fungi species against SDHI fungicides are known in field populations and lab mutants. The above-mentioned SDHI fungicides are in general cross-resistant and have been grouped under the FRAC code No 7 in the revised FRAC code list visible on the FRAC site (http://www.frac.info/frac/work/work_sdhi.htm).

FRAC code No 7 (October 2012)

| Chemical Group | Fungicides (common name) |
| --- | --- |
| Phenyl-benzamides | Benodanil |
|  | Flutolanil |
|  | Mepronil |
| Pyridinyl-ethyl-benzamides | Fluopyram |
| Furan-carboxamides | Fenfuram |
| Oxathiin-carboxamides | Carboxin |
|  | Oxycarboxin |
| Thiazole-carboxamides | Thifluzamide |
| Pyrazole-carboxamides | Bixafen |
|  | Fluxapyroxad |
|  | Furametpyr |
|  | Isopyrazam |
|  | Penflufen |
|  | Penthiopyrad |
|  | Sedaxane |
| Pyridine-carboxamides | Boscalid |

In a particular embodiment of the invention, compound of formula (I) or salt thereof are used for treating plants curatively and/or preventively against at least one resistant strain of fungi which is resistant to at least one SDHI (succinate dehydrogenase inhibitor) fungicide which is a benzamide or carboxamide derivative.

In a particular embodiment of the invention, compound of formula (I) or salt thereof are used for treating plants curatively and/or preventively against at least one resistant strain of fungi which is resistant to at least one SDHI (succinate dehydrogenase inhibitor) fungicide which belongs to a chemical group selected in the list of phenyl-benzamides, pyridinyl-ethyl-benzamides, furan-carboxamides, oxathiin-carboxamides, thiazole-carboxamides, pyrazole-carboxamides and pyridine-carboxamides.

In a particular embodiment of the invention, compound of formula (I) or salt thereof are used for treating plants curatively and/or preventively against at least one resistant strain of fungi which is resistant to at least one SDHI (succinate dehydrogenase inhibitor) fungicide selected in the list consisting of benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, trifluzamid, benzovindiflupyr, isofetamid.

A list of fungal species with resistance reports towards SDHI fungicides and the corresponding mutations in the succinate dehydrogenase gene is regularly published by the FRAC, and visible on their site http://www.frac.info/frac/work/work_sdhi.htm.

The fungal species with resistance reports cited in the FRAC updated March 2012 document are *Ustilago maydis. Mycosphaerella graminicola. Aspergillus oryzae, Botrytis cinerea, Botrytis elliptica, Alternaria alternata, Corynespora cassiicola, Didymella bryoniae, Podosphaera xanthii, Sclerotinia sclerotiorum* and *Stemphylium botryose*, and the resistance mechanism (subunit mutation) are the following:

| Species name | Resistance mechanism (subunit-mutation) |
| --- | --- |
| *Ustilago maydis* | B-H257L |
| *Mycosphaerella graminicola* | B-H267Y/R/L; B-I269V; C-H152R; C-N86K; D-H139E and many others |

-continued

| Species name | Resistance mechanism (subunit-mutation) |
|---|---|
| *Aspergillus oryzae* | B-H249Y/L/N; C-T90I; D-D124E |
| *Botrytis cinerea* | B-P225L/T/F; B-H272Y/R/L; B-N230I; D-H132R |
| *Botrytis elliptica* | B-H272Y/R |
| *Alternaria alternata* | B-H277Y/R; C-H134R; D-D123E; D-H133R |
| *Corynespora cassiicola* | B-H287Y/R; C-S73P; D-S89P |
| *Didymella bryoniae* | B-H277R/Y |
| *Podosphaera xanthii* | B-H->Y |
| *Sclerotinia sclerotiorum* | D-H132R |
| *Stemphylium botryose* | B-P225L; H272Y/R |

In a particular embodiment of the invention, compound of formula (I) or salt thereof are used for treating plants curatively and/or preventively against at least one resistant strain of fungi, resistant to at least one SDHI (succinate dehydrogenase inhibitor) fungicide, selected in the list consisting of *Ustilago maydis, Mycosphaerella graminicola, Aspergillus oryzae, Botrytis cinerea, Botrytis elliptica, Alternaria alternata, Corynespora cassiicola, Didymella bryoniae, Podosphaera xanthii, Sclerotinia sclerotiorum* and *Stemphylium botryose.*

In a particular embodiment of the invention, compound of formula (I) or salt thereof are used for treating plants curatively and/or preventively against at least one resistant strain of fungi resistant to at least one SDHI (succinate dehydrogenase inhibitor) fungicide wherein the fungi resistance to fungicide is conferred by a mutation on the amino acid at position 73, 86, 89, 90, 123, 124, 132, 133, 134, 139, 152, 225, 230, 249, 257, 267, 269, 272, 277 or 287 in the sequence of the succinate dehydrogenase from said fungi. More particularly on mutation at position 225.

In a particular embodiment of the invention, compound of formula (I) or salt thereof are used for treating plants curatively and/or preventively against at least one resistant strain of fungi resistant to at least one SDHI (succinate dehydrogenase inhibitor) fungicide wherein the fungi resistance to fungicide is conferred by a mutation selected from the list of the following mutations in the amino acid sequence of the succinate dehydrogenase from said fungi: B-H257L; B-H267Y/R/L; B-I269V; C-H152R; C-N86K; D-H139E; B-H249Y/L/N; C-T90I; D-D124E; B-P225L/T/F/H; B-H272Y/R/L; B-N230I; D-H132R; B-H277Y/R; C-H134R; D-D123E; D-H133R; B-H287Y/R; C-S73P; D-S89P; D-H132R. More particularly B-P225LT/F/H.

The application rates of the compounds of formula (I) used in the method of the present invention are generally from 0.005 to 0.5 kg/ha, preferably 0.01 to 0.2 kg/ha, in particular 0.02 to 0.1 kg/ha.

For seed treatment, the application rates are generally from 0.001 to 250 g/kg of seeds, preferably 0.01 to 100 g/kg, in particular 0.01 to 50 g/kg.

The compounds of formula (I) used in the method of the present invention can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, e.g. by extending the active ingredient with solvents and/or carriers, if desired using emulsifiers and dispersants, it being possible also to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water, carriers such as ground natural minerals (e. g. kaolins, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates) and dispersants such as lignosulfite waste liquors and methylcellulose.

Suitable surfactants are the alkali metal salts, alkaline earth metal salts and ammonium salts of aromatic sulfonic acids, e.g. ligno-, phenol-, naphthalene- and dibutyinaphthalenesulfonic acid, and of fatty acids, alkyl- and alkylarylsulfonates, alkyl, lauryl ether and fatty alcohol sulfates, and salts of sulfate hexa-, hepta- and octadecanols, or of fatty alcohol glycol ethers, condensates of sulfonate naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds of formula (I) I with a solid carrier.

Granules (e.g. coated granules, impregnated granules or homogeneous granules) are usually prepared by binding the active ingredient, or active ingredients, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of the compound. The active ingredients are employed in a purity of from 90% to 100%, preferably 95% to 100% (according to NMR spectrum or HPLC).

The compounds according to the invention may also be present in combination with other active compounds, for example with herbicides, insecticides, growth regulators, fungicides or else with fertilizers. In many cases, a mixture of the compounds of formula (I), or of the compositions comprising them, in the use form as growth promoters with other active compounds results in a broader spectrum of activity.

The following list of fungicides in combination with which the compounds according to the invention can be used is intended to illustrate the possible combinations, but not to impose any limitation: The active ingredients specified herein by their "common name" are known and described, for example, in the Pesticide Manual or can be searched in the internet (e.g. http://www.alanwood.net/pesticides). Where a compound (A) or a compound (B) can be present in tautomeric form, such a compound is understood hereinabove and herein below also to include, where applicable, corresponding tautomeric forms, even when these are not specifically mentioned in each case.

1) Inhibitors of the ergosterol biosynthesis, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulfate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazol, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafine, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl]1H-imidazole-1-carbothioate, (1.65) Pyrisoxazole.

2) Inhibitors of the respiratory chain at complex I or II, for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1 RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxyl)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) Isofetamid.

3) Inhibitors of the respiratory chain at complex III, for example (3.1) ametoctradin, (3.2) amisulbrom, (3.3) azoxystrobin, (3.4) cyazofamid, (3.5) coumethoxystrobin, (3.6) coumoxystrobin, (3.7) dimoxystrobin, (3.8) enoxastrobin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethylidene}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.27) Fenaminostrobin, (3.28) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.29) methyl (2E)-2-{2-[({cyclopropyl[(4-methoxyphenyl)imino]methyl}sulfanyl)methyl]phenyl}-3-methoxyacrylate, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide; (3.33) (2E,3Z)-5-{[1-(4-chlorophenyl)-1H-pyrazol-3-yl]oxy}-2-(methoxyimino)-N,3-dimethylpent-3-enamide.

4) Inhibitors of the mitosis and cell division, for example (4.1) benomyl, (4.2) carbendazim, (4.3) chlorfenazole, (4.4) diethofencarb, (4.5) ethaboxam, (4.6) fluopicolide, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable to have a multisite action, for example (5.1) bordeaux mixture, (5.2) captafol, (5.3) captan, (5.4) chlorothalonil, (5.5) copper hydroxide, (5.6) copper naphthenate, (5.7) copper oxide, (5.8) copper oxychloride, (5.9) copper (2+) sulfate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulfur and sulfur preparations including calcium polysulfide, (5.31) thiram, (5.32) tolylfluanid, (5.33) zineb, (5.34) ziram, (5.35) anilazine.

6) Compounds capable to induce a host defence, for example (6.1) acibenzolar-S-methyl, (6.2) isotianil, (6.3) probenazole, (6.4) tiadinil, (6.5) laminarin.

7) Inhibitors of the amino acid and/or protein biosynthesis, for example (7.1) andoprim, (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline, (7.9) oxytetracycline, (7.10) streptomycin.

8) Inhibitors of the ATP production, for example (8.1) fentin acetate, (8.2) fentin chloride, (8.3) fentin hydroxide, (8.4) silthiofam.

9) Inhibitors of the cell wall synthesis, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate, (9.10) polyoxin B.

10) Inhibitors of the lipid and membrane synthesis, for example (10.1) biphenyl, (10.2) chloroneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of the melanin biosynthesis, for example (11.1) carpropamid, (11.2) diclocymet, (11.3) fenoxanil, (11.4) phthalide, (11.5) pyroquilon, (11.6) tricyclazole, (11.7) 2,2,2-trifluoroethyl {3-methyl-1-[(4-methylbenzoyl) amino]butan-2-yl}carbamate.

12) Inhibitors of the nucleic acid synthesis, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazol, (12.9) metalaxyl, (12.10) metalaxyl-M (mefenoxam), (12.11) ofurace, (12.12) oxadixyl, (12.13) oxolinic acid, (12.14) octhilinone.

13) Inhibitors of the signal transduction, for example (13.1) chlozolinate, (13.2) fenpiclonil, (13.3) fludioxonil, (13.4) iprodione, (13.5) procymidone, (13.6) quinoxyfen, (13.7) vinclozolin, (13.8) proquinazid.

14) Compounds capable to act as an uncoupler, for example (14.1) binapacryl, (14.2) dinocap, (14.3) ferimzone, (14.4) fluazinam, (14.5) meptyldinocap.

15) Further compounds, for example (15.1) benthiazole, (15.2) bethoxazin, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat metilsulfate, (15.17) diphenylamine, (15.18) ecomate, (15.19) fenpyrazamine, (15.20) flumetover, (15.21) fluoroimide, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.37) oxamocarb, (15.38) oxyfenthiin, (15.39) pentachlorophenol and salts, (15.40) phenothrin, (15.41) phosphorous acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrine, (15.48) tebufloquin, (15.49) teclofta-lam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulfonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl) ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl) thiophene-2-sulfonohydrazide, (15.74) 5-fluoro-2-[(4-fluorobenzyl)oxy]pyrimidin-4-amine, (15.75) 5-fluoro-2-[(4-methylbenzyl)oxy]pyrimidin-4-amine, (15.76) 5-methyl-6-octyl[1,2,4]triazolo[1,5-a]pyrimidin-7-amine, (15.77) ethyl (2Z)-3-amino-2-cyano-3-phenylacrylate, (15.78) N'-(4-{[3-(4-chlorobenzyl)-1,2,4-thiadiazol-5-yl] oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulfate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulfonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulfanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulfanyl)-1-{[rel(2R,3S)-3-(2-chlorophenyl)-2-(2,4-difluorophenyl)oxiran-2-yl]methyl}-1H-1,2,4-triazole, (15.136) 5-(allylsulfanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) Abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro- 2-etylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazole-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazol-5-amine; (15.183) 2-[4-(4-chlorophenoxy)-2-(trifluoromethyl)phenyl]-1-(1H-1,2,4-triazol-1-yl)propan-2-ol, (15.184) 2-[4-(4-chlorophenoxy)-2-(trifluoromethyl)phenyl]-1-(1H-1,2,4-triazol-1-yl)butan-2-ol, (15.185) 2-[4-(4-chlorophenoxy)-2-(trifluoromethyl)phenyl]-1-(1H-1,2,4-triazol-1-yl)pentan-2-ol, (15.186) 2-[2-chloro-4-(4-chlorophenoxy)phenyl]-1-(1H-1,2,4-triazol-1-yl)butan-2-ol, (15.187) 2-[2-chloro-4-(2,4-dichlorophenoxy)phenyl]-1-(1H-1,2,4-triazol-1-yl)propan-2-ol, (15.188) 9-fluoro-2,2-dimethyl-5-(quinolin-3-yl)-2,3-dihydro-1,4-benzoxazepine, (15.189) 2-{2-fluoro-6-[(8-fluoro-2-methylquinolin-3-yl)oxy]phenyl}propan-2-ol, (15.190) 2-{2-[(7,8-difluoro-2-methylquinolin-3-yl)oxy]-6-fluorophenyl}propan-2-ol.

All named mixing partners of the classes (1) to (15) can, if their functional groups enable this, optionally form salts with suitable bases or acids.

The precise amount of compound according to the invention may depend upon the particular plant species being treated. This may be determined by the man skilled in the art with a few experiments and may vary in plant responses depending upon the total amount of compound used, as well as the particular plant species, which is being treated. Of course, the amount of compound should be non-phytotoxic with respect of the plant being treated.

Although a particularly suitable method of application of the compounds used in the process of this invention is directly to the foliage, fruits and stems of plants, such compounds may be also applied to the soil in which the plants are growing. They will then be root-absorbed to a sufficient extent so as to result in plant responses in accordance with the teachings of this invention. The compounds of the invention may also be provided to the treated crop by seed-treatment.

The compounds of the invention are able to regulate plant growth both for monocotyledonous or dicotyledonous plants.

Among the plants that can be protected by the method according to the invention, mention can be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural crops such as *Rosaceae* sp. (for examples rose) and forest crops; oil-rich plants such as *Brassicaceae* sp. (for instance oilseed rape), *Asteraceae* sp. (for instance sunflower); grasses such as turf, as well as genetically modified homologues of these crops.

The compounds of the invention are particularly suitable for regulating plant growth of cotton, vine, cereals (such as wheat, rice, barley, triticale), corn, soybean, oilseed rape, sunflower, turf, horticultural crops, shrubs, fruit-trees and fruit-plants (such as apple-tree, peer-tree, citrus, banana, coffea, strawberry plant, raspberry plant), vegetables, particularly cereals, corn, oilseed rape, shrubs, fruit-trees and fruit-plants, vegetables and vines.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as Rosaceae sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterruliceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids. Examples of nematode resistant plants are described in e.g. U.S. patent application Ser. Nos. 11/765,491, 11/765,494, 10/926,819, 10/782,020, 12/032, 479, 10/783,417, 10/782,096, 11/657,964, 12/192,904, 11/396,808, 12/166,253, 12/166,239, 12/166,124, 12/166, 209, 11/762,886, 12/364,335, 11/763,947, 12/252,453, 12/209,354, 12/491,396, 12/497,221, 12/644,632, 12/646, 004, 12/701,058, 12/718,059, 12/721,595, 12/638,591 and in WO11/002992, WO11/014749, WO11/103247, WO11/103248.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curt. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS as described in for example EP 0837944, WO 00/66746, WO 00/66747, WO02/26995, WO 11/000498. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044, WO 11/076877, WO 11/076882, WO 11/076885, WO 11/076889, WO 11/076892. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024782, WO 11/076345, WO2012058223 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a doublestranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.
2) plants which contain a stress tolerance enhancing transgene capable of reducing the expression and/or the activity of the PARG encoding genes of the plants or plants cells, as described e.g. in WO 2004/090140.
3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026, WO 97/20936, WO 10/012796, WO 10/003701

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213,
3) transgenic plants which produce hyaluronan, as for example disclosed in WO 2006/032538, WO 2007/039314, WO 2007/039315, WO 2007/039316, JP 2006304779, and WO 2005/012529.
4) transgenic plants or hybrid plants, such as onions with characteristics such as 'high soluble solids content', 'low pungency' (LP) and/or 'long storage' (LS), as described in U.S. patent application Ser. No. 12/020, 360 and 61/054,026.
5) Transgenic plants displaying an increase yield as for example disclosed in WO 1/095528

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549
b) Plants, such as cotton plants, containing an altered form of rsw2 or rsw3 homologous nucleic acids as described in WO 2004/053219
c) Plants, such as cotton plants, with increased expression of sucrose phosphate synthase as described in WO 01/17333
d) Plants, such as cotton plants, with increased expression of sucrose synthase as described in WO 02/45485
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
f) Plants, such as cotton plants, having fibers with altered reactivity, e.g. through the expression of N-acetylglucosaminetransferase gene including nodC and chitin synthase genes as described in WO 2006/136351 WO 1/089021, WO2012074868

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. Nos. 5,969,169, 5,840,946 or 6,323,392 or 6,063,947 b) Plants such as oilseed rape plants, producing oil having a low linolenic acid content as described in U.S. Pat. Nos. 6,270,828, 6,169,190, 5,965,755, or WO 11/060946.

c) Plant such as oilseed rape plants, producing oil having a low level of saturated fatty acids as described e.g. in U.S. Pat. No. 5,434,283 or U.S. patent application Ser. No. 12/668,303 d) Plants such as oilseed rape plants, producing oil having an aleter glucosinolate content as described in WO2012075426.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230, WO09/068313, WO10/006732 and WO2012090499.

Plants or plant cultivars (that can be obtained by plant biotechnology methods such as genetic engineering) which may also be treated according to the invention are plants, such as Tobacco plants, with altered post-translational protein modification patterns, for example as described in WO 10/121818 and WO 10/145846

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.irc.it/gmp_browse.aspx and http://www.agbios.com/dbase.php).

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US2002120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control —herbicide tolerance, deposited as PTA-6233, described in WO2005/103266 or US2005216969); Event 3006-210-23 (cotton, insect control—herbicide tolerance, deposited as PTA-6233, described in US2007143876 or WO2005/103266); Event 3272 (corn, quality trait, deposited as PTA-9972, described in WO2006098952 or US2006230473); Event 40416 (corn, insect control—herbicide tolerance, deposited as ATCC PTA-11508, described in WO2011/075593); Event 43A47 (corn, insect control —herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US2006162007 or WO2004053062); Event B 16 (corn, herbicide tolerance, not deposited, described in US2003126634); Event BPS-CV127-9 (soybean, herbicide tolerance, deposited as NCIMB No. 41603, described in WO2010/080829); Event CE43-67B (cotton, insect control, deposited as DSM ACC2724, described in US2009217423 or WO2006/128573); Event CE44-69D (cotton, insect control, not deposited, described in US20100024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US2006130175 or WO2004039986); Event COT202 (cotton, insect control, not deposited, described in US2007067868 or WO2005054479); Event COT203 (cotton, insect control, not deposited, described in WO2005/054480); Event DAS40278 (corn, herbicide tolerance, deposited as ATCC PTA-10244, described in WO2011/022469); Event DAS-59122-7 (corn, insect control—herbicide tolerance, deposited as ATCC PTA 11384, described in US2006070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US2009137395 or WO2008/112019); Event DP-305423-1 (soybean, quality trait, not deposited, described in US2008312082 or WO2008/054747); Event DP-32138-1 (corn, hybridization system, deposited as ATCC PTA-9158, described in US20090210970 or WO2009/103049); Event DP-356043-5 (soybean, herbicide tolerance, deposited as ATCC PTA-8287, described in US20100184079 or WO2008/002872); Event EE-1 (brinjal, insect control, not deposited, described in WO2007/091277); Event FI 117 (corn, herbicide tolerance, deposited as ATCC 209031, described in US2006059581 or WO 1998/044140); Event GA21 (corn, herbicide tolerance, deposited as ATCC 209033, described in US2005086719 or WO1998/044140); Event GG25 (corn, herbicide tolerance, deposited as ATCC 209032, described in US2005188434 or WO 1998/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US2010050282 or WO2007/017186); Event GJ11 (corn, herbicide tolerance, deposited as ATCC 209030, described in US2005188434 or WO 1998/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB41159, described in US2004172669 or WO2004/074492); Event JOPLIN1 (wheat, disease tolerance, not deposited, described in US2008064032); Event LL27 (soybean, herbicide tolerance, deposited as NCIMB41658, described in WO2006/108674 or US2008320616); Event LL55 (soybean, herbicide tolerance, deposited as NCIMB 41660, described in WO2006/108675 or US2008196127); Event LLcotton25 (cotton, herbicide tolerance, deposited as ATCC PTA-3343, described in WO2003013224 or US2003097687); Event LLRICE06 (rice, herbicide tolerance, deposited as ATCC-23352, described in U.S. Pat. No. 6,468,747 or WO2000/026345); Event LLRICE601 (rice, herbicide tolerance, deposited as ATCC PTA-2600, described in US20082289060 or WO2000/026356); Event LY038 (corn, quality trait, deposited as ATCC PTA-5623, described in US2007028322 or WO2005061720); Event MIR162 (corn, insect control, deposited as PTA-8166, described in US2009300784 or WO2007/142840); Event MIR604 (corn, insect control, not deposited, described in US2008167456 or WO2005103301); Event MON15985 (cotton, insect control, deposited as ATCC PTA-2516, described in US2004-250317 or WO2002/100163); Event MON810 (corn, insect control, not deposited, described in US2002102582); Event MON863 (corn, insect control, deposited as ATCC PTA-2605, described in WO2004/011601 or US2006095986); Event MON87427 (corn, pollination control, deposited as ATCC PTA-7899, described in WO2011/062904); Event MON87460 (corn, stress tolerance, deposited as ATCC PTA-8910, described in WO2009/111263 or US20110138504); Event MON87701 (soybean, insect control, deposited as ATCC PTA-8194, described in US2009130071 or WO2009/064652); Event MON87705 (soybean, quality trait—herbicide tolerance, deposited as ATCC PTA-9241, described in US20100080887 or WO2010/037016); Event MON87708 (soybean, herbicide tolerance, deposited as ATCC PTA9670, described in WO2011/034704); Event MON87754 (soybean, quality trait, deposited as ATCC PTA-9385, described in WO2010/024976); Event MON87769 (soybean, quality trait, deposited as ATCC PTA-8911, described in US20110067141 or WO2009/102873); Event MON88017 (corn, insect control—herbicide tolerance, deposited as ATCC PTA-5582, described in US2008028482 or WO2005/059103); Event MON88913 (cotton, herbicide tolerance, deposited as ATCC PTA-4854, described in WO2004/072235 or US2006059590); Event MON89034 (corn, insect control, deposited as ATCC PTA-7455, described in WO2007/140256 or US2008260932); Event MON89788 (soybean, herbicide tolerance, deposited as ATCC PTA-6708, described in US2006282915 or WO2006/130436); Event MS11 (oilseed rape, pollination control—herbicide tolerance, deposited as ATCC PTA-850 or PTA-2485, described in WO2001/031042); Event MS8, (oilseed rape, pollination control—herbicide tolerance, deposited as ATCC PTA-730, described in WO2001/041558 or US2003188347); Event NK603 (corn, herbicide tolerance, deposited as ATCC PTA-2478, described in US2007-292854); Event PE-7 (rice, insect control, not deposited, described in WO2008/114282); Event RF3, (oilseed rape, pollination control—herbicide tolerance, deposited as ATCC PTA-730, described in WO2001/041558 or US2003188347); Event RT73 (oilseed rape, herbicide tolerance, not deposited, described in WO2002/036831 or US2008070260); Event T227-1 (sugar beet, herbicide tolerance, not deposited, described in WO2002/44407 or US2009265817); Event T25 (corn, herbicide tolerance, not deposited, described in US2001029014 or WO2001/051654); Event T304-40 (cotton, insect control—herbicide tolerance, deposited as ATCC PTA-8171, described in US2010077501 or WO2008/122406); Event T342-142 (cotton, insect control, not deposited, described in WO2006/128568); Event TC 1507 (corn, insect control—herbicide tolerance, not deposited, described in US2005039226 or WO2004/099447); Event VIP1034 (corn, insect control—herbicide tolerance, deposited as ATCC PTA-3925, described in WO2003/052073), Event 32316 (corn, insect control—herbicide tolerance, deposited as PTA-11507, described in WO2011/153186A1), Event 4114 (corn, insect control-herbicide tolerance, deposited as PTA-11506, described in WO2011/084621), event EE-GM3/FG72 (soybean, herbicide tolerance, ATCC Accession No PTA-11041, WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No PTA-11028, WO2012/033794A2), event MON-87712-4 (soybean, quality trait, ATCC Accession No PTA-10296, WO2012/051199A2), event DAS-44406-6 (soybean, stacked herbicide tolerance, ATCC Accession No PTA-11336, WO2012/075426A1), event DAS-14536-7 (soybean, stacked herbicide tolerance, ATCC Accession No PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, W02012075429A2).

The present invention further relates to the use of a compound of formula (I)

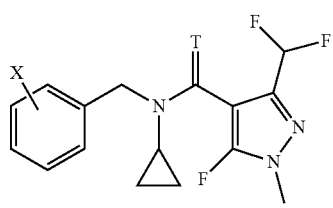

(I)

wherein T represents an oxygen or a sulfur atom and X is selected from the list of 2-isopropyl, 2-cyclopropyl, 2-tert-butyl, 5-chloro-2-ethyl, 5-chloro-2-isopropyl, 2-ethyl-5-fluoro, 5-fluoro-2-isopropyl, 2-cyclopropyl-5-fluoro, 2-cyclopentyl-5-fluoro, 2-fluoro-6-isopropyl, 2-ethyl-5-methyl, 2-isopropyl-5-methyl, 2-cyclopropyl-5-methyl, 2-tert-butyl-5-methyl, 5-chloro-2-(trifluoromethyl), 5-methyl-2-(trifluoromethyl),2-chloro-6-(trifluoromethyl), 3-chloro-2-fluoro-6-(trifluoromethyl), 2-ethyl, 2-trimethylsilyl and 2-ethyl-4,5-dimethyl, or an agrochemically acceptable salt thereof, for treating plants curatively and/or preventively against at least one resistant strain of fungi.

Preference is given to the use, for treating plants curatively and/or preventively against at least one resistant strain of fungi, of a compound of formula (I) selected from the group consisting of:

N-cyclopropyl-3-(difluoromethyl)-5-fluoro-N-(2-isopropylbenzyl)-1-methyl-1H-pyrazole-4-carboxamide (compound A1), N-cyclopropyl-N-(2-cyclopropylbenzyl)-3-(difluoromethyl)-5-fluoro-1-methyl-1H-pyrazole-4-carboxamide (compound A2), N-(2-tert-butylbenzyl)-N-cyclopropyl-3-(difluoromethyl)-5-fluoro-1-methyl-1H-pyrazole-4-carboxamide (compound A3), N-(5-chloro-2-ethylbenzyl)-N-cyclopropyl-3-(difluoromethyl)-5-fluoro-1-methyl-1H-pyrazole-4-carboxamide (compound A4), N-(5-chloro-2-isopropylbenzyl)-N-cyclopropyl-3-(difluoromethyl)-5-fluoro-1-methyl-1H-pyrazole-4-carboxamide (compound A5), N-cyclopropyl-3-(difluoromethyl)-N-(2-ethyl-5-fluorobenzyl)-5-fluoro-1-methyl-1H-pyrazole-4-carboxamide (compound A6), N-cyclopropyl-3-(difluoromethyl)-5-fluoro-N-(5-fluoro-2-isopropylbenzyl)-1-methyl-1H-pyrazole-4-carboxamide (compound A7), N-cyclopropyl-N-(2-cyclopropyl-5-fluorobenzyl)-3-(difluoromethyl)-5-fluoro-1-methyl-1H-pyrazole-4-carboxamide (compound A8), N-(2-cyclopentyl-5-fluorobenzyl)-N-cyclopropyl-3-(difluoromethyl)-5-fluoro-1-methyl-1H-pyrazole-4-carboxamide (compound A9), N-cyclopropyl-3-(difluoromethyl)-5-fluoro-N-(2-fluoro-6-isopropylbenzyl)-1-methyl-1H-pyrazole-4-carboxamide (compound A10), N-cyclopropyl-3-(difluoromethyl)-N-(2-ethyl-5-methylbenzyl)-5-fluoro-1-methyl-1H-pyrazole-4-carboxamide (compound A11), N-cyclopropyl-3-(difluoromethyl)-5-fluoro-N-(2-isopropyl-5-methylbenzyl)-1-methyl-1H-pyrazole-4-carboxamide (compound A12), N-cyclopropyl-N-(2-cyclopropyl-5-methylbenzyl)-3-(difluoromethyl)-5-fluoro-1-methyl-1H-pyrazole-4-carboxamide (compound A13), N-(2-tert-butyl-5-methylbenzyl)-N-cyclopropyl-3-(difluoromethyl)-5-fluoro-1-methyl-1H-pyrazole-4-carboxamide (compound A14), N-[5-chloro-2-(trifluoromethyl)benzyl]-N-cyclopropyl-3-(difluoromethyl)-5-fluoro-1-methyl-1H-pyrazole-4-carboxamide (compound A15), N-cyclopropyl-3-(difluoromethyl)-5-fluoro-1-methyl-N-[5-methyl-2-(trifluoromethyl)benzyl]-1H-pyrazole-4-carboxamide (compound A16), N-[2-chloro-6-(trifluoromethyl)benzyl]-N-cyclopropyl-3-(difluoromethyl)-5-fluoro-1-methyl-1H-pyrazole-4-carboxamide (compound A17), N-[3-chloro-2-fluoro-6-(trifluoromethyl)benzyl]-N-cyclopropyl-3-(difluoromethyl)-5-fluoro-1-methyl-1H-pyrazole-4-carboxamide (compound A18).

N-cyclopropyl-3-(difluoromethyl)-N-(2-ethyl-4,5-dimethylbenzyl)-5-fluoro-1-methyl-1H-pyrazole-4-carboxamide (compound A19), N-cyclopropyl-3-(difluoromethyl)-5-fluoro-N-(2-isopropylbenzyl)-1-methyl-1H-pyrazole-4-carbothio-amide (compound A20), N-cyclopropyl-3-(difluoromethyl)-N-(2-ethylbenzyl)-5-fluoro-1-methyl-1H-pyrazole-4-carboxamide (compound A21), and N-cyclopropyl-3-(difluoromethyl)-5-fluoro-1-methyl-N-[2-(trimethylsilyl)benzyl]-1H-pyrazole-4-carboxamide (compound A22).

In a particular embodiment, the invention refers to the use of a compound of formula (I) as herein defined for treating plants curatively and/or preventively against at least one resistant strain of fungi, wherein the strain of fungi is resistant to at least one SDHI (succinate dehydrogenase inhibitor) fungicide.

In a particular embodiment, the invention refers to the use of a compound of formula (I) as herein defined for treating plants curatively and/or preventively against at least one resistant strain of fungi, wherein the strain of fungi is resistant to at least one SDHI (succinate dehydrogenase inhibitor) fungicide which is a benzamide or carboxamide derivative.

In a particular embodiment, the invention refers to the use of a compound of formula (I) as herein defined for treating plants curatively and/or preventively against at least one resistant strain of fungi, wherein the SDHI fungicide belongs to a chemical group selected in the list of phenyl-benzamides, pyridinyl-ethyl-benzamide, furan-carboxamides, oxathiin-carboxamides, thiazole-carboxamides, pyrazole-carboxamides and pyridine-carboxamides.

In a particular embodiment, the invention refers to the use of a compound of formula (I) as herein defined for treating plants curatively and/or preventively against at least one resistant strain of fungi, wherein the SDHI fungicide is selected in the list consisting of benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, trifluzamid, benzovindiflupyr, isofetamid.

In a particular embodiment, the invention refers to the use of a compound of formula (I) as herein defined for treating plants curatively and/or preventively against at least one resistant strain of fungi, wherein the strain of fungi resistant to SDHI fungicides is selected in the list consisting of *Ustilago maydis, Mycosphaerella graminicola, Aspergillus oryzae, Botrytis cinerea, Botrytis elliptica, Alternaria alternata, Corynespora cassiicola, Didymella bryoniae, Podosphaera xanthii, Sclerotinia sclerotiorum* and *Stemphylium botryose*

In a particular embodiment, the compound of formula (I) as herein defined is applied to the plants or to the locus in which they grow at an application rate of from about 0.005 kg/ha to about 0.5 kg/ha of compound of formula (I), preferably 0.01 to 0.2 kg/ha, in particular 0.02 to 0.1 kg/ha.

In another particular embodiment, the compound of formula (I) as herein defined is applied as seed treatment at an application rate of from 0.001 to 250 g/kg of seeds, preferably 0.01 to 100 g/kg, in particular 0.01 to 50 g/kg.

In a particular embodiment, the plant is selected from the group consisting of cotton, vine, cereals (such as wheat, rice, barley, triticale), corn, soybean, oilseed rape, sunflower, turf, horticultural crops, shrubs, fruit-trees and fruit-plants (such as apple-tree, peer-tree, citrus, banana, coffea, strawberry plant, raspberry plant), vegetables, particularly cereals, corn, oilseed rape, shrubs, fruit-trees and fruit-plants, vegetables and vines.

N-cyclopropyl amides of formula (I) wherein T represents an oxygen atom, can be prepared by condensation of a substituted N-cyclopropyl benzylamine with 3-(difluoromethyl)-5-fluoro-1-methyl-1H-pyrazole-4-carbonyl chloride according to WO-2007/087906 (process P1) and WO-2010/130767 (process P1-step 10).

Substituted N-cyclopropyl benzylamines are known or can be prepared by known processes such as the reductive amination of a substituted aldehyde with cyclopropanamine (*J. Med. Chem.*, 2012, 55 (1), 169-196) or by nucleophilic substitution of a substituted benzyl alkyl (or aryl)sulfonate or a substituted benzyl halide with cyclopropanamine (*Bioorg. Med. Chem.*, 2006, 14, 8506-8518 and WO-2009/140769).

3-(difluoromethyl)-5-fluoro-1-methyl-1H-pyrazole-4-carbonyl chloride can be prepared according to WO-2010/130767 (process P1-steps 9 or 11)

N-cyclopropyl thioamides of formula (I) wherein T represents a sulfur atom, can be prepared by thionation of a N-cyclopropyl amide of formula (I) wherein T represents a oxygen atom, according to WO-2009/016220 (process P1) and WO-2010/130767 (process P3).

The following examples illustrate in a non limiting manner the preparation of the compounds of formula (I) according to the invention.

Preparation of N-cyclopropyl-3-(difluoromethyl)-5-fluoro-N-(2-isopropylbenzyl)-1-methyl-1H-pyrazole-4-carboxamide (Compound A1)

Step A: preparation of N-(2-isopropylbenzyl)cyclopropanamine

To a solution of 55.5 g (971 mmol) of cyclopropanamine in 900 mL of methanol, are successively added 20 g of 3 Å molecular sieves and 73 g (1.21 mol) of acetic acid. 72 g (486 mmol) of 2-isopropyl-benzaldehyde are then added dropwise and the reaction mixture is further heated at reflux for 4 hours. The reaction mixture is then cooled to 0° C. and 45.8 g (729 mmol) of sodium cyanoborohydride are added by portion in 10 min and the reaction mixture is stirred again for 3 hours at reflux. The cooled reaction mixture is filtered over a cake of diatomaceous earth. The cake is washed abundantly by methanol and the methanolic extracts are concentrated under vacuum. Water is then added to the residue and the pH is adjusted to 12 with 400 mL of a 1 N aqueous solution of sodium hydroxide. The watery layer is extracted with ethyl acetate, washed by water (2×300 mL) and dried over magnesium sulfate to yield 81.6 g (88%) of N-(2-isopropylbenzyl)cyclopropanamine as a yellow oil used as such in the next step.

The hydrochloride salt can be prepared by dissolving N-(2-isopropylbenzyl)cyclopropanamine in diethyl-ether (1.4 mL/g) at 0° C. followed by addition of a 2 M solution of hydrochloric acid in diethylether (1.05 eq.). After a 2 hours stirring, N-(2-isopropylbenzyl)cyclopropanamine hydrochloride (1:1) is filtered off, washed by diethylether and dried under vacuum at 40° C. for 48 hours. Mp (melting point)=149° C.

Step B: preparation of N-cyclopropyl-3-(difluoromethyl)-5-fluoro-N-(2-isopropylbenzyl)-1-methyl-1H-pyrazole-4-carboxamide To 40.8 g (192 mmol) of N-(2-isopropylbenzyl)cyclopropanamine in 1 L of dry tetrahydrofurane are added at room temperature, 51 mL (366 mmol) of triethylamine. A solution of 39.4 g (174 mmol) of 3-(difluoromethyl)-5-fluoro-1-methyl-1H-pyrazole-4-carbonyl chloride in 800 mL of dry tetrahydrofurane is then added dropwise while maintaining the temperature below 34° C. The reaction mixture is heated at reflux for 2 hours then left overnight at room temperature. Salts are filtered off and the filtrate is concentrated under vacuum to yield 78.7 g of a brown oil. Column chromatography on silica gel (750 g-gradient n-heptane/ethyl acetate) yields 53 g (71% yield) of N-cyclopropyl-3-(difluoromethyl)-5-fluoro-N-(2-isopropylbenzyl)-1-methyl-1H-pyrazole-4-carboxamide as a yellow oil that slowly crystallizes. Mp=76-79° C.

In the same way, compounds A2 to A19, A21, A22 can be prepared according to the preparation described for compound A1.

Preparation of N-cyclopropyl-3-(difluoromethyl)-5-fluoro-N-(2-isopropylbenzyl)-1-methyl-1H-pyrazole-4-carbothioamide (COMPOUND A20)

A solution of 14.6 g (65 mmol) of phosphorus pentasulfide and 48 g (131 mmol) of N-cyclopropyl-3-(difluoromethyl)-5-fluoro-N-(2-isopropylbenzyl)-1-methyl-1H-pyrazole-4-carboxamide in 500 ml of dioxane are heated at 100° C. for 2 hours. 50 ml of water are then added and the reaction mixture is further heated at 100° C. for another hour. The cooled reaction mixture is filtered over a basic alumina cartridge. The cartridge is washed by dichloromethane and the combined organic extracts are dried over magnesium sulfate and concentrated under vacuum to yield 55.3 g of an orange oil. The residue is tritured with a few mL of diethylether until crystallisation occurs. Crystals are filtered off and dried under vacuum at 40° C. for 15 hours to yield 46.8 g (88% yield) of N-cyclopropyl-3-(difluoromethyl)-5-fluoro-N-(2-isopropylbenzyl)-1-methyl-1H-pyrazole-4-carbothioamide. Mp=64-70° C.

Table 1 provides the log P and NMR data ($^1$H) of compounds A1 to A20.

In table 1, the log P values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones). lambda-max-values were determined using UV-spectra from 200 nm to 400 nm and the peak values of the chromatographic signals.

| Cmpd | logP | NMR |
|---|---|---|
| A1 | 3.35 | $^1$H NMR (500 MHz, CHCl$_3$-d): δ ppm 0.64 (bs, 4H), 1.21 (d, J = 6.60 Hz, 6H), 2.44-2.80 (m, 1H), 3.01-3.29 (m, 1H), 3.78 (s, 3H), 4.76 (bs, 2H), 6.89 (t, J = 54.70 Hz, 1H), 7.12-7.33 (m, 4H). |
| A2 | 3.44 | $^1$H NMR (500 MHz, CHCl$_3$-d): δ ppm 0.47-0.77 (m, 6H) 0.80-1.04 (m, 2H), 1.92 (bs, 1H), 2.66 (bs, 1H), 3.80 (s, 3H), 4.92 (bs, 2H), 6.90 (t, J = 54.50 Hz, 1H), 7.01-7.25 (m, 4H). |
| A3 | 4.06 | $^1$H NMR (500 MHz, CHCl$_3$-d): δ ppm 0.61 (bs, 4H), 1.46 (s, 9H), 2.77-2.98 (m, 1H), 3.89 (s, 3H), 5.05 (bs, 2 H), 6.91 (t, J = 54.70 Hz, 1H), 7.20 (bs, 3H), 7.35-7.48 (m, 1H). |
| A4 | 3.76 | $^1$H NMR (300 MHz, CHCl$_3$-d): δ ppm 0.65-0.69 (m, 4H), 1.21 (t, 3H), 2.62-2.64 (m, 3H), 3.81 (s, 3H), 4.70 (s, 2H), 6.85 (t, J = 54.6 Hz, 1H), 7.04-7.22 (m, 3H). |
| A5 | 4.09 | $^1$H NMR (500 MHz, CHCl$_3$-d): δ ppm 0.63-0.73 (m, 4H), 1.22 (d, J = 6.92 Hz, 6H), 2.59-2.87 (m, 1H), 2.98-3.30 (m, 1H), 3.82 (s, 3H), 4.74 (bs, 2H), 6.88 (t, J = 54.40 Hz, 1H), 7.20-7.27 (m, 3H). |
| A6 | 3.41 | $^1$H NMR (300 MHz, CHCl$_3$-d): δ ppm 0.65-0.66 (m, 4H), 1.21 (t, 3H), 2.62 (q, 2H), 2.64 (bs, 1H), 3.81 (s, 3H), 4.71 (s, 2H), 6.86 (t, J = 54.6 Hz, 1H), 6.89-6.95 (m, 2H), 7.13-7.18 (m, 1H). |
| A7 | 3.70 | $^1$H NMR (300 MHz, CHCl$_3$-d): δ ppm 0.65-0.69 (m, 4H), 1.22 (d, 6H), 2.69 (bs, 1H), 3.10-3.14 (m, 1H), 3.81 (s, 3H), 4.75 (s, 2H), 6.86 (t, J = 54.6 Hz, 1H), 6.88-6.93 (m, 2H), 7.23-7.28 (m, 1H). |
| A8 | 3.46 | $^1$H NMR (300 MHz, CHCl$_3$-d): δ ppm 0.60-0.66 (m, 6H), 0.89-0.95 (m, 2H), 1.82-1.84 (m, 1H), 2.73 (bs, 1H), 3.81 (s, 3H), 4.89 (s, 2H), 6.68-6.99 (m, 4H). |
| A9 | 4.21 | $^1$H NMR (300 MHz, CHCl$_3$-d): δ ppm 0.64-0.68 (m, 4H), 1.56-1.62 (m, 2H), 1.62-1.70 (m, 2H), 1.76-1.83 (m, 2H), 1.96-2.05 (m, 2H), 2.71 (bs, 1H), 3.13-3.19 (m, 1H), 3.81 (s, 3H), 4.76 (s, 2H), 6.86 (t, J = 54.0 Hz, 1H), 6.87-6.97 (m, 2H), 7.23-7.28 (m, 1H). |
| A10 | 3.65 | $^1$H NMR (400 MHz, CHCl$_3$-d): δ ppm 0.65 (bs, 4H), 1.21 (d, J = 6.75 Hz, 5H), 2.29-2.59 (m, 1H), 3.00-3.36 (m, 1H), 3.79 (s, 3H), 4.83 (s, 2H), 6.68-7.06 (m, 2H), 7.13 (d, J = 7.78 Hz, 1H), 7.27-7.33 (m, 1H). |
| A11 | 3.70 | $^1$H NMR (500 MHz, CHCl$_3$-d): δ ppm 0.65 (bs, 4H), 2.31 (s, 3H), 2.64 (m, 1H), 3.81 (s, 3H), 4.73 (bs, 2H), 6.89 (t, J = 54.6 Hz, 1H), 7.01-7.14 (m, 3H). |
| A12 | 3.99 | $^1$H NMR (500 MHz, CHCl$_3$-d): δ ppm 0.66 (bs, 4H), 1.22 (d, J = 6.97 Hz, 6H), 2.31 (s, 3H), 2.54-2.75 (m, 1H), 2.99-3.25 (m, 1H), 3.81 (s, 3H), 4.75 (bs, 2H), 6.89 (t, J = 53.90 Hz, 1H), 7.01-7.23 (m, 3H). |
| A13 | 3.76 | $^1$H NMR (500 MHz, CHCl$_3$-d): δ ppm 0.61-0.68 (m, 6H), 0.80-1.00 (m, 2H), 1.74-2.00 (m, 1H), 2.31 (s, 3H), 2.53-2.82 (m, 1H), 3.81 (s, 3H), 4.89 (bs, 2H), 6.83 (t, J = 54.80 Hz, 1H), 6.91-7.06 (m, 3H). |
| A14 | 4.36 | $^1$H NMR (500 MHz, CHCl$_3$-d): δ ppm 0.62 (m, 4H), 1.44 (s, 9H), 2.28 (s, 3H), 2.74-3.02 (m, 1H), 3.83 (bs, 3H), 5.02 (bs, 2H), 6.85 (t, J = 54.40 Hz, 1 H), 7.01 (bs, 1H), 7.21-7.29 (m, 2 H). |
| A15 | 3.80 | $^1$H NMR (500 MHz, CHCl$_3$-d): δ ppm 0.50-0.67 (m, 4H), 2.81 (bs, 1H), 3.78 (s, 3H), 4.85 (bs, 2H), 6.78 (t, J = 55.00 Hz, 1H), 7.20-7.29 (m, 2H), 7.54 (d, J = 8.17 Hz, 1H). |
| A16 | 3.78 | $^1$H NMR (500 MHz, CHCl$_3$-d): δ ppm 0.55-0.70 (m, 4H), 2.37 (s, 3H), 2.72-3.04 (m, 1H), 3.83 (bs, 3H), 4.91 (bs, 2H), 6.86 (t, J = 54.50 Hz, 1H), 7.10-7.20 (m, 2H), 7.54 (d, J = 7.89 Hz, 1H). |
| A17 | 3.46 | $^1$H NMR (500 MHz, CHCl$_3$-d): δ ppm 0.47-0.64 (m, 4H), 2.29-2.55 (m, 1H), 3.80 (s, 3H), 5.05 (s, 2H), 6.95 (t, J = 54.40 Hz, 1H), 7.40 (t, J = 7.86 Hz, 1H), 7.60-7.70 (dd, 2H). |
| A18 | 3.62 | $^1$H NMR (500 MHz, CHCl$_3$-d): δ ppm 0.50-0.74 (m, 4H), 2.45-2.71 (m, 1H), 3.81 (s, 3H), 4.99 (s, 2H), 6.91 (t, J = 54.40 Hz, 1H), 7.45-7.57 (m, 2H). |
| A19 | 4.04 | $^1$H NMR (500 MHz, CHCl$_3$-d): δ ppm 0.65 (bs, 4H), 1.20 (t, J = 7.43 Hz, 3H), 2.22 (s, 3H), 2.24 (s, 3H), 2.58-2.64 (m, 2H), 3.80 (s, 3H), 4.70 (bs, 2H), 6.89 (t, J = 54.70 Hz, 3H), 6.98 (bs, 2H). |
| A20 | 4.36 | $^1$H NMR (500 MHz, CHCl$_3$-d): δ ppm 0.55-0.84 (m, 4H), 1.27 (d, J = 6.97 Hz, 6H), 2.73-2.85 (m, 1H), 3.04-3.23 (m, 1H), 3.80 (s, 3H), 4.60-5.06 (m, 1H), 6.99-7.38 (m, 5H). |

The following examples are illustrative of methods of plant growth regulation according to the invention, but should not be understood as limiting the said instant invention.

EXAMPLE I

Lack of Cross Resistance in Highly Boscalid-Resistant Field Isolated

*Botrytis cinerea* boscalid-resistant populations were collected from the field and characterized by sequencing the SDHB gene which encodes the subunit B of succinate dehydrogenase. Four to five strains with SDHB_P225H, F substitutions were retained for subsequent sensitivity assays in microtiter plate. IC50 of test compounds were determined and resistance factors (RF) calculated as the ratio of IC50 mutant/IC50 WT (Bo47). The activity of compounds of formula (I) according to the invention was compared to Boscalid, Fluxapyroxad, Penthiopyrad and Isopyrazam (Table 1). Strains giving a RF below 10 were considered sensitive, moderately resistant when RF was comprised between 10 and 50, resistant above 50.

Our results nicely demonstrated that strains harboring P225H and F substitutions remained sensitive to compounds of formula (I) according to the invention whereas they became moderately resistant to isopyrazam and resistant to other tested SDHi inhibitors.

Additionally, one tested compound (Compound A18) was seen to be always more active on strains with P225 substitutions than on wild type strain. These results emphasize the potential of compounds of formula (I) according to the invention as resistance breakers of fungi strains resistant to SDHI fungicide, and particularly to strains having SDHB_P225H,F substitutions.

TABLE 1

Cellular sensitivity of carboxamide resistant strains

| mutation | BOTRCI strains | BOSCALID | FLUXAPYROXAD | PENTHIOPYRAD | ISOPYRAZAM | Compound A3 | Compound A1 | Compound A18 | Compound A5 |
|---|---|---|---|---|---|---|---|---|---|
| P225F | 08BC1554 | >171 | 197.2 | 78.3 | 48.4 | 1.8 | 2.4 | 0.4 | 1.4 |
| P225F | 08BC1557 | >171 | 135.6 | 114.1 | 42.9 | 1.2 | 1.8 | 0.3 | 1.3 |
| P225F | 08BC1558 | >171 | 131.5 | 113.0 | 37.9 | 2.2 | 3.0 | 0.5 | 1.6 |
| P225F | 09BC2615 | >171 | 89.1 | 68.1 | 32.8 | 1.0 | 1.6 | 0.4 | 0.8 |
| P225H | 09BC2640 | >171 | 103.0 | 62.0 | 19.7 | 0.9 | 1.3 | 0.4 | 1.3 |
| P225H | 09BC2648 | >171 | 127.9 | 168.2 | 25.1 | 1.0 | 0.9 | 0.4 | 0.8 |
| P225H | 09BC2649 | >171 | 134.2 | 103.8 | 30.7 | 1.7 | 1.1 | 0.5 | 0.9 |
| P225H | 09BC2652 | >171 | 104.7 | 82.6 | n.d. | 1.1 | 1.1 | 0.3 | 1.0 |

EXAMPLE 2

Mitochondrial Sensitivity of Boscalid Resistant Mutants

Compounds activity was investigated at the level of the mitochondrial target and compared to other SDH inhibitors. The 3884 isolate was collected from field and SDHB gene sequencing revealed a P225H substitution.

Mitochondria were extracted according to Cramer et al. (1983) Analytical biochemistry, 128, 384-392 and the mycelium prepared according to Fritz et al., (1993). Agronomie 13, 225-230 except that spore's incubation was pursued for 48 hours. SDH activity was measured by following DCPIP (2,6-dichlorphenol-indophenol) reduction at 595 nm overtime. To test SDH inhibitors, mitochondria were incubated with test compounds for 20 min prior the initiation of the reaction. Inhibition of the succinate-ubiquinone redutase activity was expressed as pI50 which represents the −log 10 of the concentration inhibiting DCPIP reduction by 50% (IC50). pI50 obtained on mutated mitochondria were compared to those calculated for the Bo47 WT strain used as the reference in these experiments.

Our results showed that pI50 obtained with compounds of formula (I) according to the invention on mitochondria extracted from the 3884 strain (P225H substitution) are always higher or equal to those obtained on the reference strain (classification A). This demonstrates that SDHB_P225H substitution does not compromise the activity of the compound of formula (I) on the Sdh complex while this mutation significantly affects the activity of other tested SDH inhibitors (pI50 reduction by more than one unit was commonly observed with other SDH inhibitors). To confirm these data, the IC50 of compounds of formula (I) according to the invention were recorded on the 3884 strain (P225H substitution) and compared to the Bo47 WT strain. As expected, compounds of formula (I) were still controlling the wild type and 3884 strains when the activity of other SDH inhibitors was impaired on the 3884 strain.

TABLE 2

Sensitivity conferred by amino acid substitutions at the mitochondrial (PI50 value) and at the cellular (IC50) levels

| | PI50 Bo47 (Wild type) | PI50 P225H3884 | Classification | IC50 Bo47 (Wild type) | IC50 P225H3884 |
|---|---|---|---|---|---|
| Compound A5 | 8.2 | 8.9 | A | 0.026 | 0.025 |
| Compound A12 | 8.4 | 9.0 | A | 0.019 | 0.028 |
| Compound A7 | 8.4 | 8.8 | A | 0.03 | 0.041 |
| Compound A21 | 8/7.5 | 8.6 | A | 0.016 | 0.03 |
| Compound A16 | 7.7 | 8.3 | A | 0.079 | 0.15 |
| Compound A1 | 7.9 | 8.5 | A | <0.006 | 0.03 |
| Compound A18 | 7.8 | 8.2 | A | 0.4 | 0.21 |
| Compound A15 | 7.8 | 8.2 | A | 0.48 | 0.43 |
| Compound A22 | 8.4 | 8.5 | A | 0.15 | 0.32 |
| Compound A17 | 8.0 | 8.5 | A | 0.11 | 0.032 |
| Compound A9 | 8.3 | 8.5 | A | 0.018 | 0.015 |
| Compound A8 | 8.1 | 8.5 | A | 0.19 | 0.12 |
| Compound A2 | 8.2 | 8.6 | A | n.d. | n.d. |
| Compound A20 | 6.2 | 7.5 | A | 2.7 | 1.5 |
| Compound A10 | 8.4 | 8.2 | B | <0.006 | 0.04 |
| Compound A6 | 8.1 | 8.6 | A | n.d. | 9.6 |
| Compound A14 | 8.3 | 8.5 | A | 0.77 | 0.58 |
| Boscalid | 7.4 | 5.3 | C | 0.28 | >20 |
| Fluxapyroxad | 8.0 | 6.2 | C | 0.049 | 7.6 |
| Penthiopyrad | 7.8 | 6.3 | C | 0.41 | 5.8 |
| Isopyrazam | 8/8.2 | 7.2 | C | n.d. | n.d. |

Classification A pI50 increase or stable compared to WT
Classification B pI50 decrease inferior or equal to 0.6 compared to WT
Classification C pI50 decrease superior to 0.6 compared to WT

The invention claimed is:

1. A method for treating plants curatively and/or preventively against at least one resistant strain of fungi, comprising applying to plants in need thereof, to the seeds from which they grow or to the locus in which they grow, a non-phytotoxic, effective plant growth promoting amount of a compound according to formula I

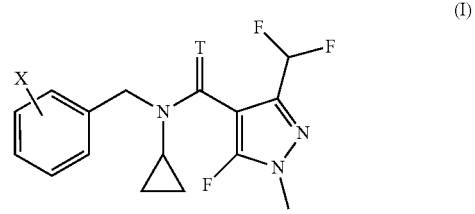

(I)

wherein T represents an oxygen or a sulfur atom and X is selected from the list of 2-isopropyl, 2-cyclopropyl, 2-tert-butyl, 5-chloro-2-ethyl, 5-chloro-2-isopropyl, 2-ethyl-5-fluoro, 5-fluoro-2-isopropyl, 2-cyclopropyl-5-fluoro, 2-cyclopentyl-5-fluoro, 2-fluoro-6-isopropyl, 2-ethyl-5-methyl, 2-isopropyl-5-methyl, 2-cyclopropyl-5-methyl, 2-tert-butyl-5-methyl, 5-chloro-2-(trifluoromethyl), 5-methyl-2-(trifluoromethyl), 2-chloro- 6-(trifluoromethyl), 3-chloro-2-fluoro-6-(trifluoromethyl), 2-ethyl, 2-trimethylsilyl and 2-ethyl-4,5-dimethyl, or an agrochemically acceptable salt thereof.

2. A method according to claim 1, wherein the compound of formula (I) is selected from the group consisting of:
N-cyclopropyl-3-(difluoromethyl)-5-fluoro-N-(2-isopropylbenzyl)-1-methyl-1H-pyrazole-4-carboxamide (compound A1),
N-cyclopropyl-N-(2-cyclopropylbenzyl)-3-(difluoromethyl)-5-fluoro-1-methyl-1H-pyrazole-4-carboxamide (compound A2),
N-(2-tert-butylbenzyl)-N-cyclopropyl-3-(difluoromethyl)-5-fluoro-1-methyl-1H-pyrazole-4-carboxamide (compound A3),
N-(5-chloro-2-ethylbenzyl)-N-cyclopropyl-3-(difluoromethyl)-5-fluoro-1-methyl-1H-pyrazole-4-carboxamide (compound A4),
N-(5-chloro-2-isopropylbenzyl)-N-cyclopropyl-3-(difluoromethyl)-5-fluoro-1-methyl-1H-pyrazole-4-carboxamide (compound A5),
N-cyclopropyl-3-(difluoromethyl)-N-(2-ethyl-5-fluorobenzyl)-5-fluoro-1-methyl-1H-pyrazole-4-carboxamide (compound A6),
N-cyclopropyl-3-(difluoromethyl)-5-fluoro-N-(5-fluoro-2-isopropylbenzyl)-1-methyl-1H-pyrazole-4-carboxamide (compound A7),
N-cyclopropyl-N-(2-cyclopropyl-5-fluorobenzyl)-3-(difluoromethyl)-5-fluoro-1-methyl-1H-pyrazole-4-carboxamide (compound A8),
N-(2-cyclopentyl-5-fluorobenzyl)-N-cyclopropyl-3-(difluoromethyl)-5-fluoro-1-methyl-1H-pyrazole-4-carboxamide (compound A9),
N-cyclopropyl-3-(difluoromethyl)-5-fluoro-N-(2-fluoro-6-isopropylbenzyl)-1-methyl-1H-pyrazole-4-carboxamide (compound A10),
N-cyclopropyl-3-(difluoromethyl)-N-(2-ethyl-5-methylbenzyl)-5-fluoro-1-methyl-1H-pyrazole-4-carboxamide (compound A11),
N-cyclopropyl-3-(difluoromethyl)-5-fluoro-N-(2-isopropyl-5-methylbenzyl)-1-methyl-1H-pyrazole-4-carboxamide (compound A12),
N-cyclopropyl-N-(2-cyclopropyl-5-methylbenzyl)-3-(difluoromethyl)-5-fluoro-1-methyl-1H-pyrazole-4-carboxamide (compound A13),
N-(2-tert-butyl-5-methylbenzyl)-N-cyclopropyl-3-(difluoromethyl)-5-fluoro-1-methyl-1H-pyrazole-4-carboxamide (compound A14),
N-[5-chloro-2-(trifluoromethyl)benzyl]-N-cyclopropyl-3-(difluoromethyl)-5-fluoro-1-methyl-1H-pyrazole-4-carboxamide (compound A15),
N-cyclopropyl-3-(difluoromethyl)-5-fluoro-1-methyl-N-[5-methyl-2-(trifluoromethyl)benzyl]-1H-pyrazole-4-carboxamide (compound A16),
N-[2-chloro-6-(trifluoromethyl)benzyl]-N-cyclopropyl-3-(difluoromethyl)-5-fluoro-1-methyl-1H-pyrazole-4-carboxamide (compound A17),
N-[3-chloro-2-fluoro-6-(trifluoromethyl)benzyl]-N-cyclopropyl-3-(difluoromethyl)-5-fluoro-1-methyl-1H-pyrazole-4-carboxamide (compound A 18),
N-cyclopropyl-3-(difluoromethyl)-N-(2-ethyl-4,5-dimethylbenzyl)-5-fluoro-1-methyl-1H-pyrazole-4-carboxamide (compound A19),
N-cyclopropyl-3-(difluoromethyl)-5-fluoro-N-(2-isopropylbenzyl)-1-methyl-1H-pyrazole-4-carbothio-amide (compound A20), N-cyclopropyl-3-(difluoromethyl)-N-(2-ethylbenzyl)-5-fluoro-1-methyl-1H-pyrazole-4-carboxamide (compound A21), and
N-cyclopropyl-3-(difluoromethyl)-5-fluoro-1-methyl-N-[2-(trimethylsilyl)benzyl]-1H-pyrazole-4-carboxamide (compound A22).

3. A method according to claim 1, wherein the strain of fungi is resistant to at least one SDHI (succinate dehydrogenase inhibitor) fungicide.

4. A method according to claim 3 wherein the SDHI fungicide belongs to a chemical group selected in the list of phenyl-benzamides, pyridinyl-ethyl-benzamide, furan-carboxamides, oxathiin-carboxamides, thiazole-carboxamides, pyrazole-carboxamides and pyridine-carboxamides.

5. A method according to claim 3 wherein the strain of fungi is resistant to at least one fungicide selected in the list consisting of benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, trifluzamid, benzovindiflupyr, isofetamid.

6. A method according to claim 1, wherein the strain of fungi resistant to SDHI fungicides is selected in the list consisting of *Ustilago maydis, Mycosphaerella graminicola, Aspergillus oryzae, Botrytis cinerea, Botrytis elliptica, Alternaria alternata, Corynespora cassiicola, Didymella bryoniae, Podosphaera xanthii, Sclerotinia sclerotiorum* and *Stemphylium botryose*.

7. A method according to claim 1, wherein the compound of formula (I) is applied to said plants or the locus in which they grow at an application rate of from about 0.005 kg/ha to about 0.5 kg/ha of compound of formula (I).

8. A method according to claim 1, wherein the compound of formula (I) is applied as seed treatment at an application rate of from 0.001 to 250 g/kg of seeds.

9. A method according to claim 1, wherein the plants are selected from the group consisting of cotton, vine, maize, soybean, oilseed rape, sunflower, turf, horticultural crops, shrubs, fruit-trees, fruit-plants, vegetables.

10. A method for treating plants curatively against at least one resistant strain of fungi comprising the step of applying to plants in need of such treatment, to the seeds from which they grow or to the locus in which they grow, a non-phytotoxic, effective plant growth promoting amount of a compound of formula (I)

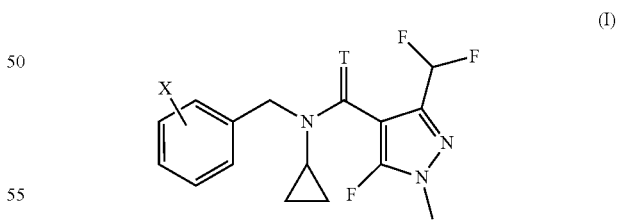

wherein T represents an oxygen or a sulfur atom and X is selected from the list of 2-isopropyl, 2-cyclopropyl, 2-tert-butyl, 5-chloro-2-ethyl, 5-chloro-2-isopropyl, 2-ethyl-5-fluoro, 5-fluoro-2-isopropyl, 2-cyclopropyl-5-fluoro, 2-cyclopentyl-5-fluoro, 2-fluoro-6-isopropyl, 2-ethyl-5-methyl, 2-isopropyl-5-methyl, 2-cyclopropyl-5-methyl, 2-tert-butyl-5-methyl, 5-chloro-2-(trifluoromethyl), 5-methyl-2-(trifluoromethyl), 2-chloro-6-(trifluoromethyl), 3-chloro-2-fluoro-6-(trifluoromethyl), 2-ethyl, 2-trimethylsilyl and 2-ethyl- 4,5-dimethyl, or an agrochemically acceptable salt thereof, to curatively treat the plants against at least one resistant strain of fungi.

11. The method according to claim 10 wherein the compound of formula (I) is selected from the group consisting of:

N-cyclopropyl-3-(difluoromethyl)-5-fluoro-N-(2-isopropylbenzyl)-1-methyl-1H-pyrazole-4-carboxamide (compound A1), N-cyclopropyl-N-(2-cyclopropylbenzyl)-3-(difluoromethyl)-5-fluoro-1-methyl-1H-pyrazole-4-carboxamide (compound A2), N-(2-tert-butylbenzyl)-N-cyclopropyl-3-(difluoromethyl)-5-fluoro-1-methyl-1H-pyrazole-4-carboxamide (compound A3), N-(5-chloro-2-ethylbenzyl)-N-cyclopropyl-3-(difluoromethyl)-5-fluoro-1-methyl-1H-pyrazole-4-carboxamide (compound A4), N-(5-chloro-2-isopropylbenzyl)-N-cyclopropyl-3-(difluoromethyl)-5-fluoro-1-methyl-1H-pyrazole-4-carboxamide (compound A5), N-cyclopropyl-3-(difluoromethyl)-N-(2-ethyl-5-fluorobenzyl)-5-fluoro-1-methyl-1H-pyrazole-4-carboxamide (compound A6), N-cyclopropyl-3-(difluoromethyl)-5-fluoro-N-(5-fluoro-2-isopropylbenzyl)-1-methyl-1H-pyrazole-4-carboxamide (compound A7), N-cyclopropyl-N-(2-cyclopropyl-5-fluorobenzyl)-3-(difluoromethyl)-5-fluoro-1-methyl-1H-pyrazole-4-carboxamide (compound A8), N-(2-cyclopentyl-5-fluorobenzyl)-N-cyclopropyl-3-(difluoromethyl)-5-fluoro-1-methyl-1H-pyrazole-4-carboxamide (compound A9), N-cyclopropyl-3-(difluoromethyl)-5-fluoro-N-(2-fluoro-6-isopropylbenzyl)-1-methyl-1H-pyrazole-4-carboxamide (compound A10), N-cyclopropyl-3-(difluoromethyl)-N-(2-ethyl-5-methylbenzyl)-5-fluoro-1-methyl-1H-pyrazole-4-carboxamide (compound A11), N-cyclopropyl-3-(difluoromethyl)-5-fluoro-N-(2-isopropyl-5-methylbenzyl)-1-methyl-1H-pyrazole-4-carboxamide (compound A12), N-cyclopropyl-N-(2-cyclopropyl-5-methylbenzyl)-3-(difluoromethyl)-5-fluoro-1-methyl-1H-pyrazole-4-carboxamide (compound A13), N-(2-tert-butyl-5-methylbenzyl)-N-cyclopropyl-3-(difluoromethyl)-5-fluoro-1-methyl-1H-pyrazole-4-carboxamide (compound A14), N-[5-chloro-2-(trifluoromethyl)benzyl]-N-cyclopropyl-3-(difluoromethyl)-5-fluoro-1-methyl-1H-pyrazole-4-carboxamide (compound A15), N-cyclopropyl-3-(difluoromethyl)-5-fluoro-1-methyl-N-[5-methyl-2-(trifluoromethyl)benzyl]-1H-pyrazole-4-carboxamide (compound A16), N-[2-chloro-6-(trifluoromethyl)benzyl]-N-cyclopropyl-3-(difluoromethyl)-5-fluoro-1-methyl-1H-pyrazole-4-carboxamide (compound A17), N-[3-chloro-2-fluoro-6-(trifluoromethyl)benzyl]-N-cyclopropyl-3-(difluoromethyl)-5-fluoro-1-methyl-1H-pyrazole-4-carboxamide (compound A18), N-cyclopropyl-3-(difluoromethyl)-N-(2-ethyl-4,5-dimethylbenzyl)-5-fluoro-1-methyl-1H-pyrazole-4-carboxamide (compound A19), N-cyclopropyl-3-(difluoromethyl)-5-fluoro-N-(2-isopropylbenzyl)-1-methyl-1H-pyrazole-4-carbothio-amide (compound A20), N-cyclopropyl-3-(difluoromethyl)-N-(2-ethylbenzyl)-5-fluoro-1-methyl-1H-pyrazole-4-carboxamide (compound A21), and N-cyclopropyl-3-(difluoromethyl)-5-fluoro-1-methyl-N-[2-(trimethylsilyl)benzyl]-1 H-pyrazole-4-carboxamide (compound A22).

12. The method according to claim 10 wherein the strain of fungi is resistant to at least one SDHI (succinate dehydrogenase inhibitor) fungicide.

13. The method according to claim 10 wherein the SDHI fungicide belongs to a chemical group selected in the list of phenyl-benzamides, pyridinyl-ethyl-benzamide, furan-carboxamides, oxathiin-carboxamides, thiazole-carboxamides, pyrazole-carboxamides, pyridine-carboxamides.

14. The method according to claim 10 wherein the strain of fungi is resistant to at least one fungicide selected in the list consisting of benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, trifluzamid, benzovindiflupyr and isofetamid.

15. The method according to claim 10 wherein the strain of fungi resistant to SDHI fungicides is selected in the list consisting of *Ustilago maydis, Mycosphaerella graminicola, Aspergillus oryzae, Botrytis cinerea, Botrytis elliptica, Alternaria alternata, Corynespora cassiicola, Didymella bryoniae, Podosphaera xanthii, Sclerotinia sclerotiorum* and *Stemphylium botryose.*

16. The method according to claim 10 wherein wherein the compound of formula (I) is applied to said plants or the locus in which they grow at an application rate of from about 0.005 kg/ha to about 0.5 kg/ha of compound of formula (I).

17. The method according to claim 10 wherein the compound of formula (I) is applied as seed treatment at an application rate of from 0.001 to 250 g/kg of seeds.

18. The method according to claim 10 wherein the plants are selected from the group consisting of cotton, vine, maize, soybean, oilseed rape, sunflower, turf, horticultural crops, shrubs, fruit-trees, fruit-plants, vegetables.

* * * * *